US007632280B2

(12) United States Patent
Hochman

(10) Patent No.: US 7,632,280 B2
(45) Date of Patent: Dec. 15, 2009

(54) METHOD AND APPARATUS FOR PERFORMING MAXILLARY SINUS ELEVATION

(76) Inventor: Mark N. Hochman, 26 Meadow Woods Rd., Lake Success, NY (US) 11020-1232

( * ) Notice: Subject to any disclaimer, the term of this patent is extended or adjusted under 35 U.S.C. 154(b) by 77 days.

(21) Appl. No.: 12/102,085

(22) Filed: Apr. 14, 2008

(65) Prior Publication Data

US 2008/0213729 A1   Sep. 4, 2008

Related U.S. Application Data

(62) Division of application No. 11/227,687, filed on Sep. 15, 2005, now Pat. No. 7,510,397.

(60) Provisional application No. 60/619,542, filed on Oct. 15, 2004.

(51) Int. Cl.
*A61C 8/00* (2006.01)
(52) U.S. Cl. .......................... 606/94; 433/172
(58) Field of Classification Search ................. 433/172, 433/173, 174, 201.1, 215; 606/92, 93, 94, 606/199
See application file for complete search history.

(56) References Cited

U.S. PATENT DOCUMENTS

| | | | | |
|---|---|---|---|---|
| 5,547,378 A | * | 8/1996 | Linkow | 433/173 |
| 5,591,171 A | * | 1/1997 | Brown | 606/94 |
| 5,711,315 A | * | 1/1998 | Jerusalmy | 128/898 |
| 5,759,033 A | * | 6/1998 | Elia | 433/173 |
| 5,899,696 A | * | 5/1999 | Shimoda | 433/173 |
| 7,125,253 B2 | * | 10/2006 | Kitamura et al. | 433/173 |
| 7,144,398 B2 | * | 12/2006 | Chern Lin et al. | 606/92 |
| 7,364,430 B2 | * | 4/2008 | Kitamura et al. | 433/173 |
| 7,510,397 B2 | * | 3/2009 | Hochman | 433/172 |
| 2003/0105469 A1 | * | 6/2003 | Karmon | 606/92 |
| 2006/0172255 A1 | * | 8/2006 | Hochman et al. | 433/144 |
| 2007/0042326 A1 | * | 2/2007 | Cardoso et al. | 433/229 |
| 2009/0104586 A1 | * | 4/2009 | Cardoso et al. | 433/229 |

FOREIGN PATENT DOCUMENTS

EP   1 174 094 A1 *   1/2002

* cited by examiner

*Primary Examiner*—Ralph A Lewis
(74) *Attorney, Agent, or Firm*—Gottlieb, Rackman & Reisman, P.C.

(57) ABSTRACT

A method and apparatus is disclosed for providing implants in the upper jaws of a person. A sleeve is inserted through the alveolar ridge to the maxillary sinus. The sleeve is used to raise the subantral membrane and form a cavity. A filler, such as a bone growth stimulant is injected through the sleeve into the cavity. In the process, the sleeve also can cut and/or condense the bone around itself so that the bone can hold an implant. Optionally, the bone growth stimulant is also introduced into the bone surrounding the sleeve. During the injection, the pressure within the sleeve or the cavity is monitored to detect and prevent the rupture of the subantral membrane.

8 Claims, 17 Drawing Sheets

Mini-balloon device inserted into the Drug Delivery Sleeve to allow a "seal" so that the SME-Mini-balloon can create a "seal" in a large opening or irregularly shaped opening.

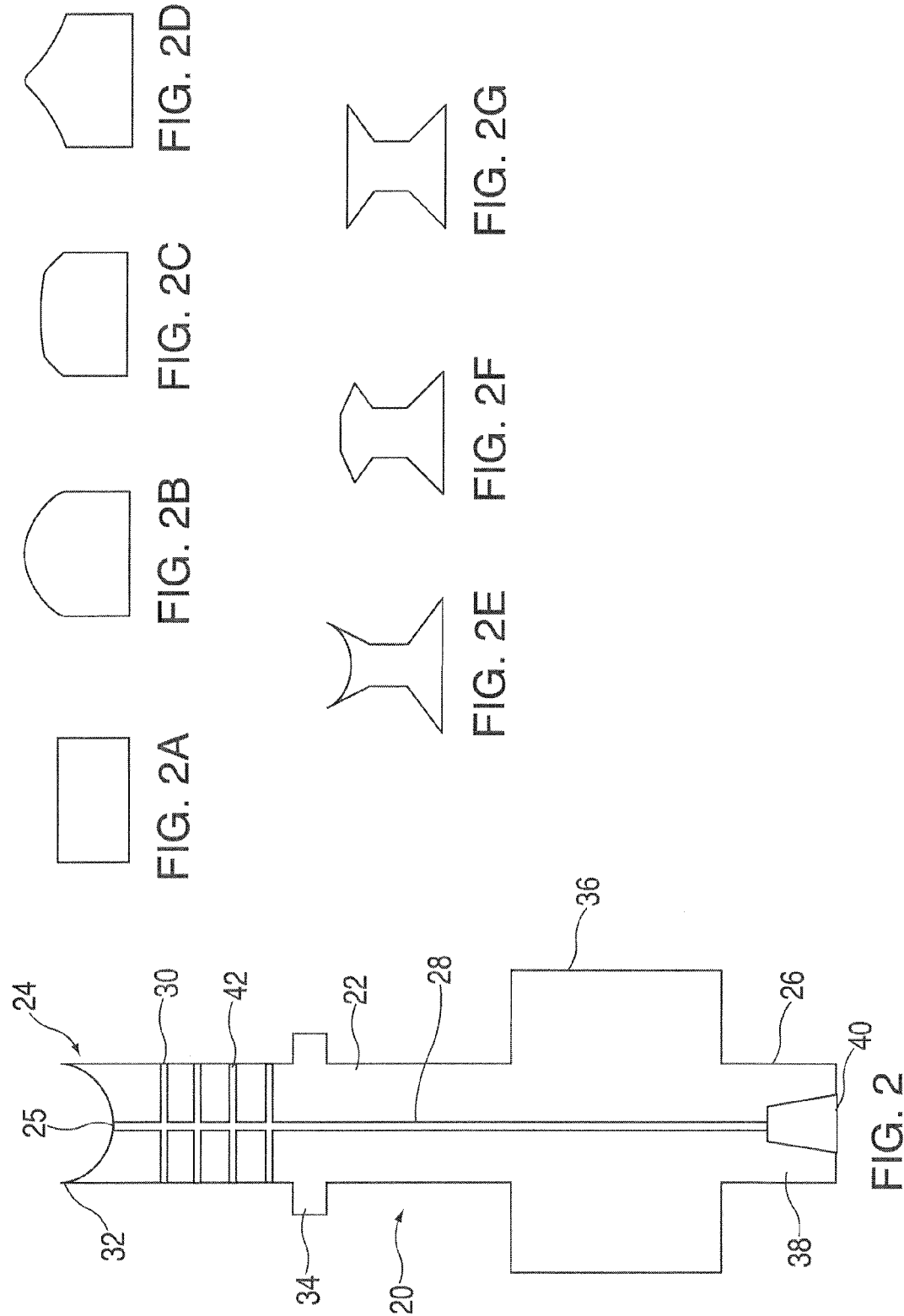

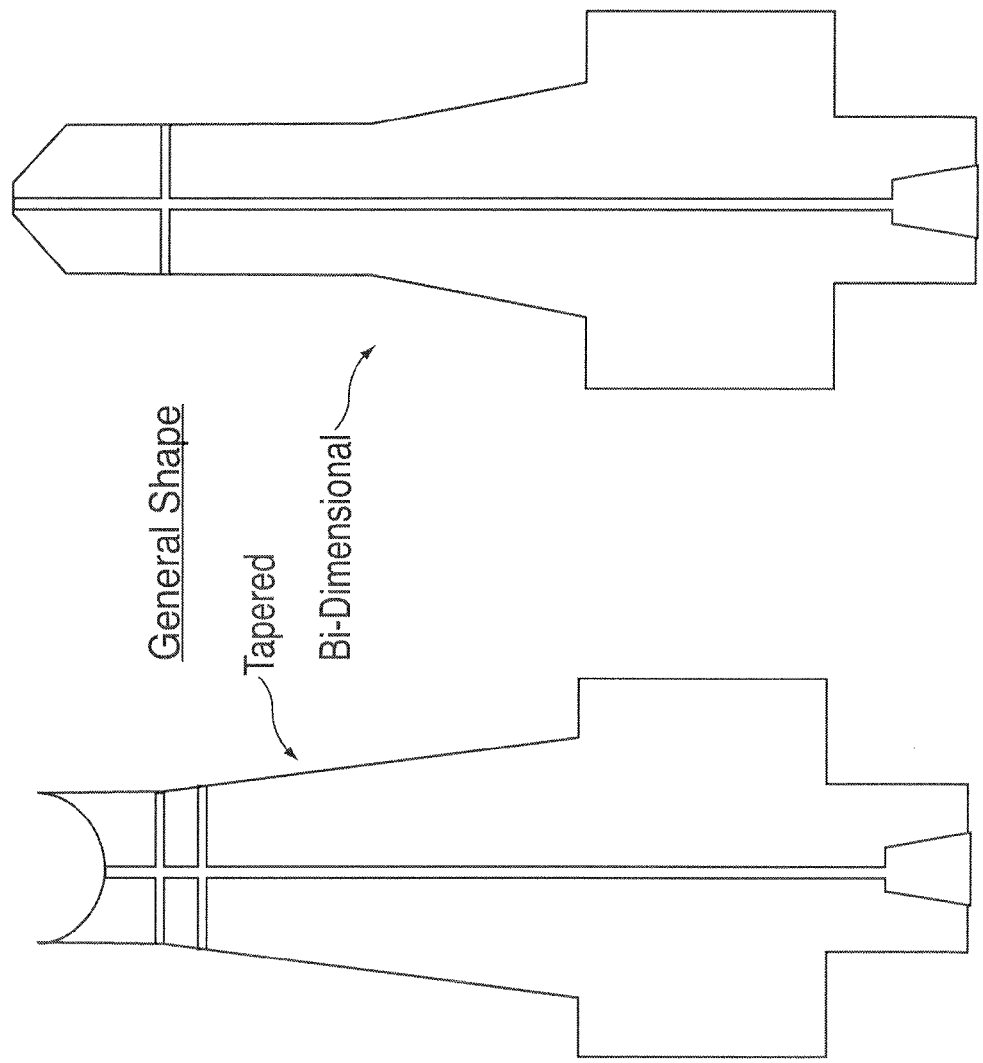

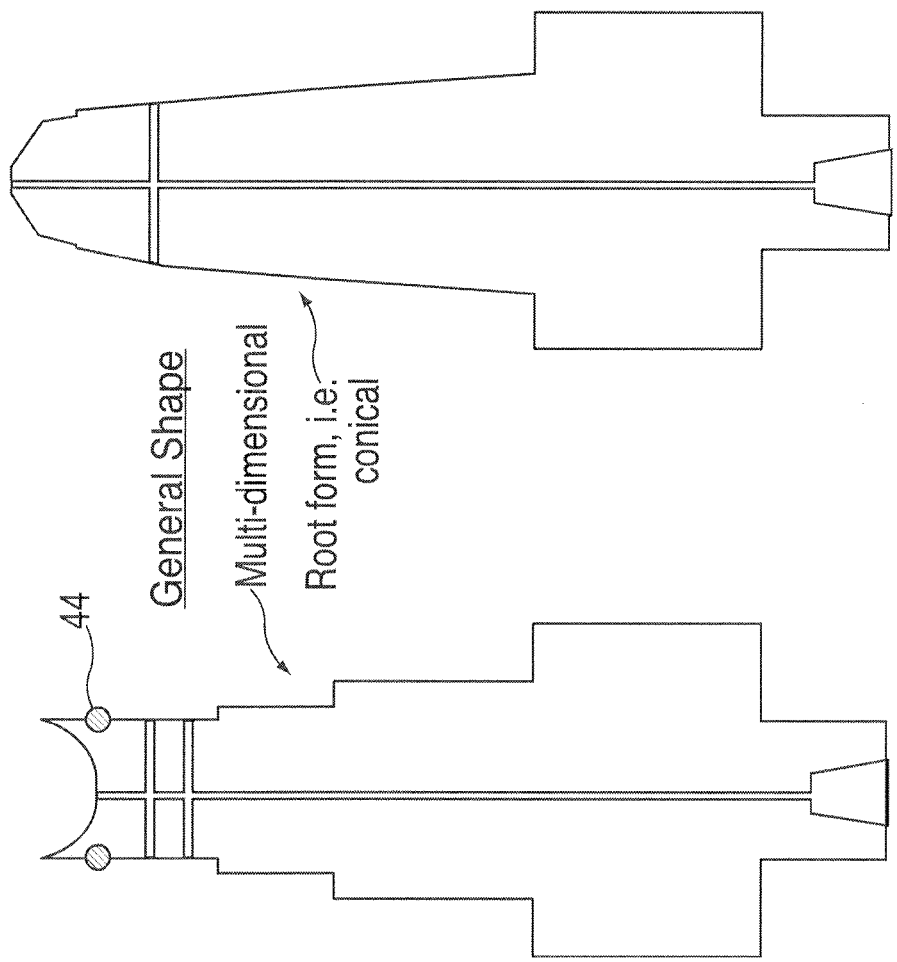

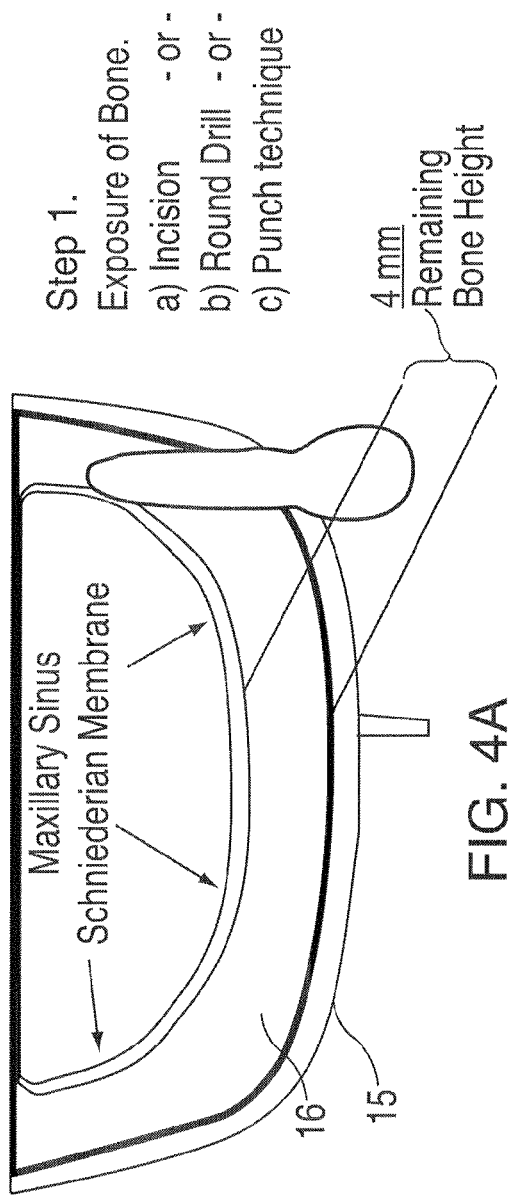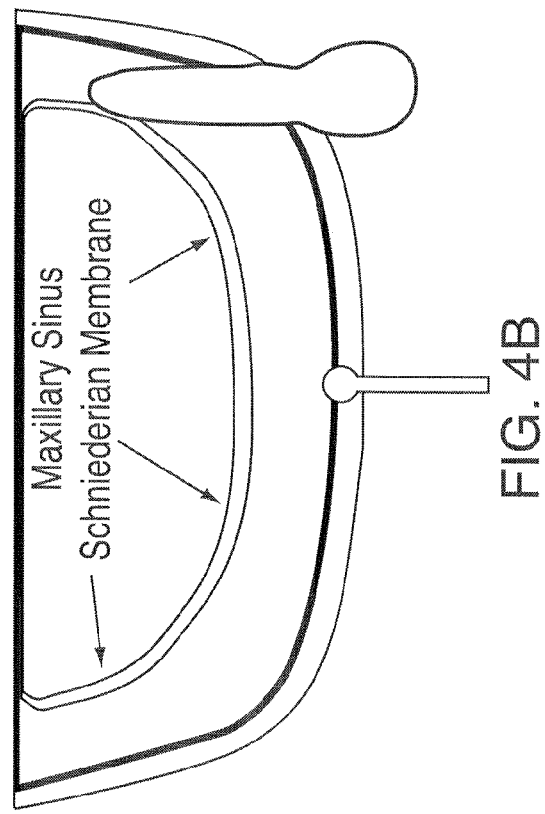

Sequence of treatment:
Step 3.
Initial Corticotomy Preparation.
a) Twist Drill 2.8mm   - or -
b) Osteotome 2.8mm   - or -
c) Ultrasonic piezo surgery Sequence of treatment:
Step 4.
Confirm distance to floor of sinus
a) Depth Gauge + Radiograph
b) Depth Gauge directly Note: 3mm are measured from ridge to floor of sinus leaving 1mm remaining.

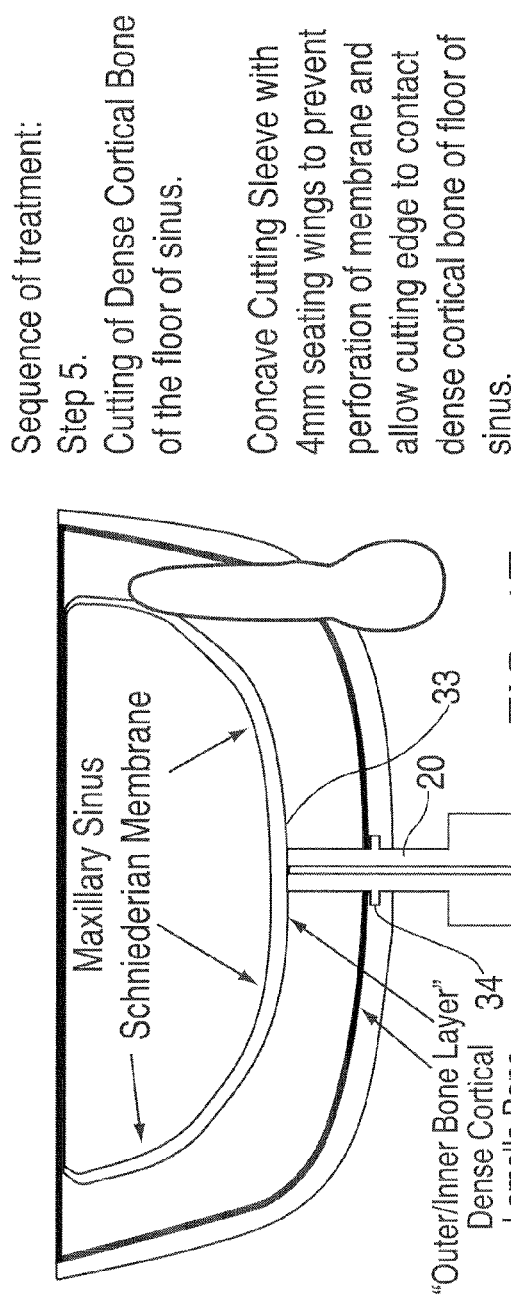

Sequence of treatment:
Step 5.
Cutting of Dense Cortical Bone of the floor of sinus.

Concave Cutting Sleeve with 4mm seating wings to prevent perforation of membrane and allow cutting edge to contact dense cortical bone of floor of sinus.

FIG. 4E

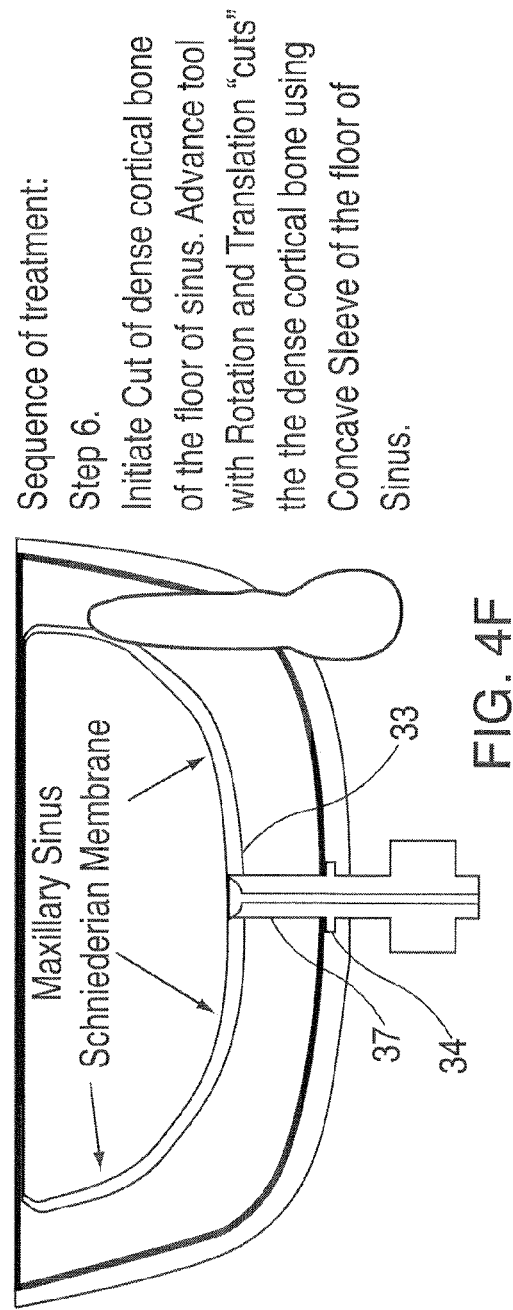

Sequence of treatment:
Step 6.
Initiate Cut of dense cortical bone of the floor of sinus. Advance tool with Rotation and Translation "cuts" the the dense cortical bone using Concave Sleeve of the floor of Sinus.

FIG. 4F

Sequence of treatment:
Step 7.

Tool can be switched to blunt Convex design of Sleeve with 5mm seating wings to prevent perforation of membrane as the tool is advanced to initiate the separation of the membrane from the surrounding bone surface.

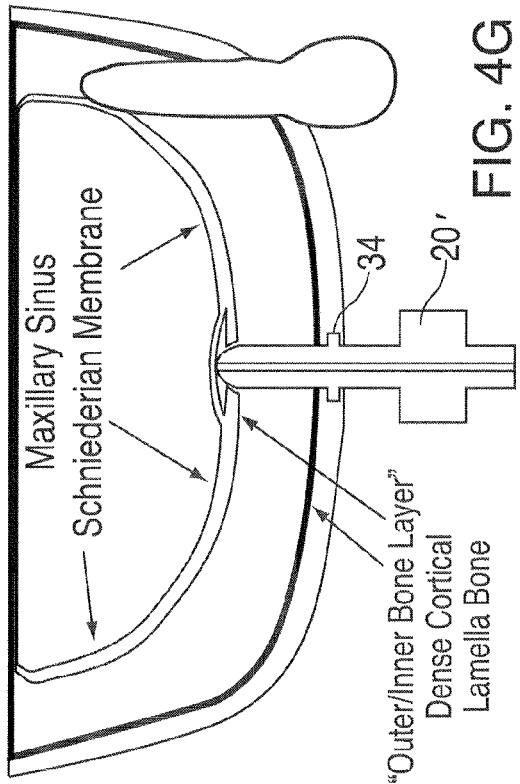

FIG. 4G

Sequence of treatment:
Step 8.

Hydrodissection by injection of solution using fluid pressure causes the membrane to further separate from floor.
Convex Sleeve with 5mm is fully seated and infusion of fluid is performed with either Sterile Saline or a Regenerative material.

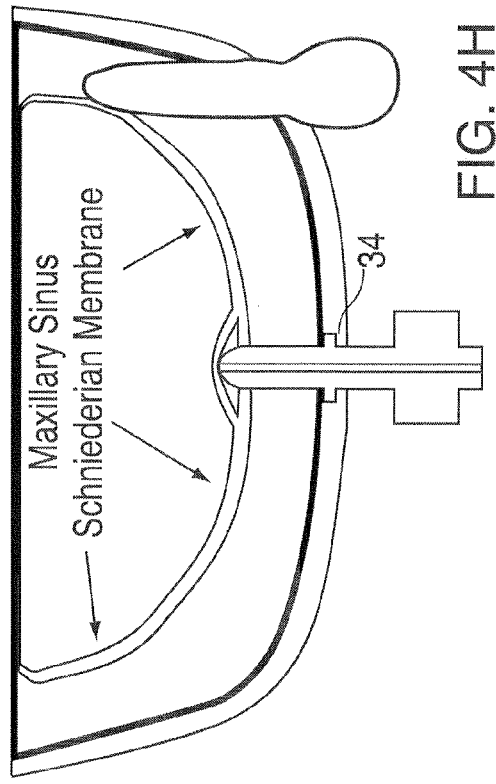

FIG. 4H

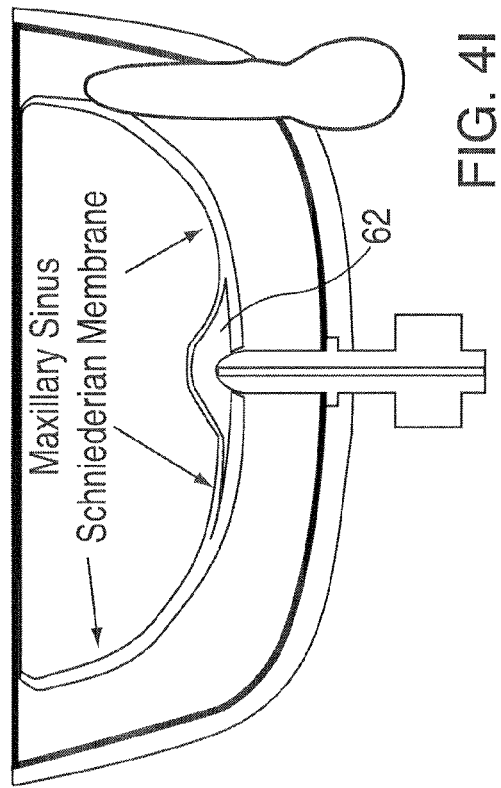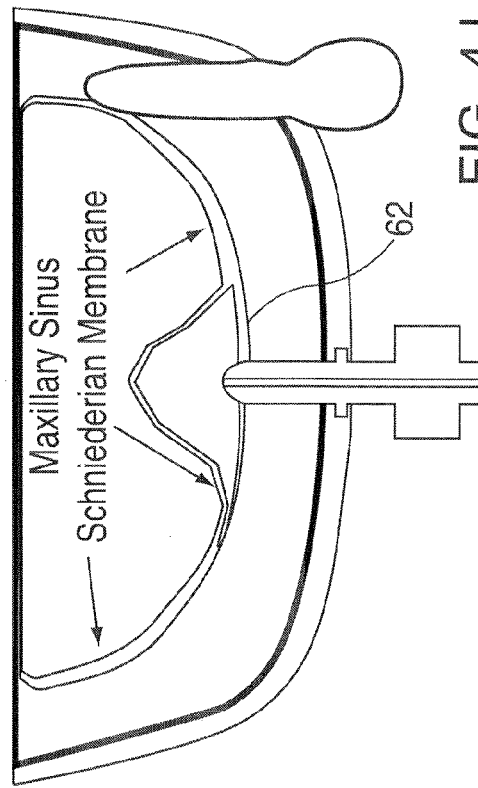

Sequence of treatment:
Step 11.

If sterile saline was used drainage of fluid now occurs after membrane elevation.

Sequence of treatment:
Step 12.

a) Placement of Regenerative material to form new bone can be placed either directly through sleeve.
- or -
b) Removal of sleeve and direct placement of material into site.

Sequence of treatment:
Step 13.

Implant placement;
a) Immediate implant placement into prepared site with elevated sinus membrane.
- or -
b) Delayed approach allowing grafted sinus to heal for a period of time and then placement of dental implant.

Sequence of treatment:
Step 14.

Radiographic confirmation of placement of bone material.

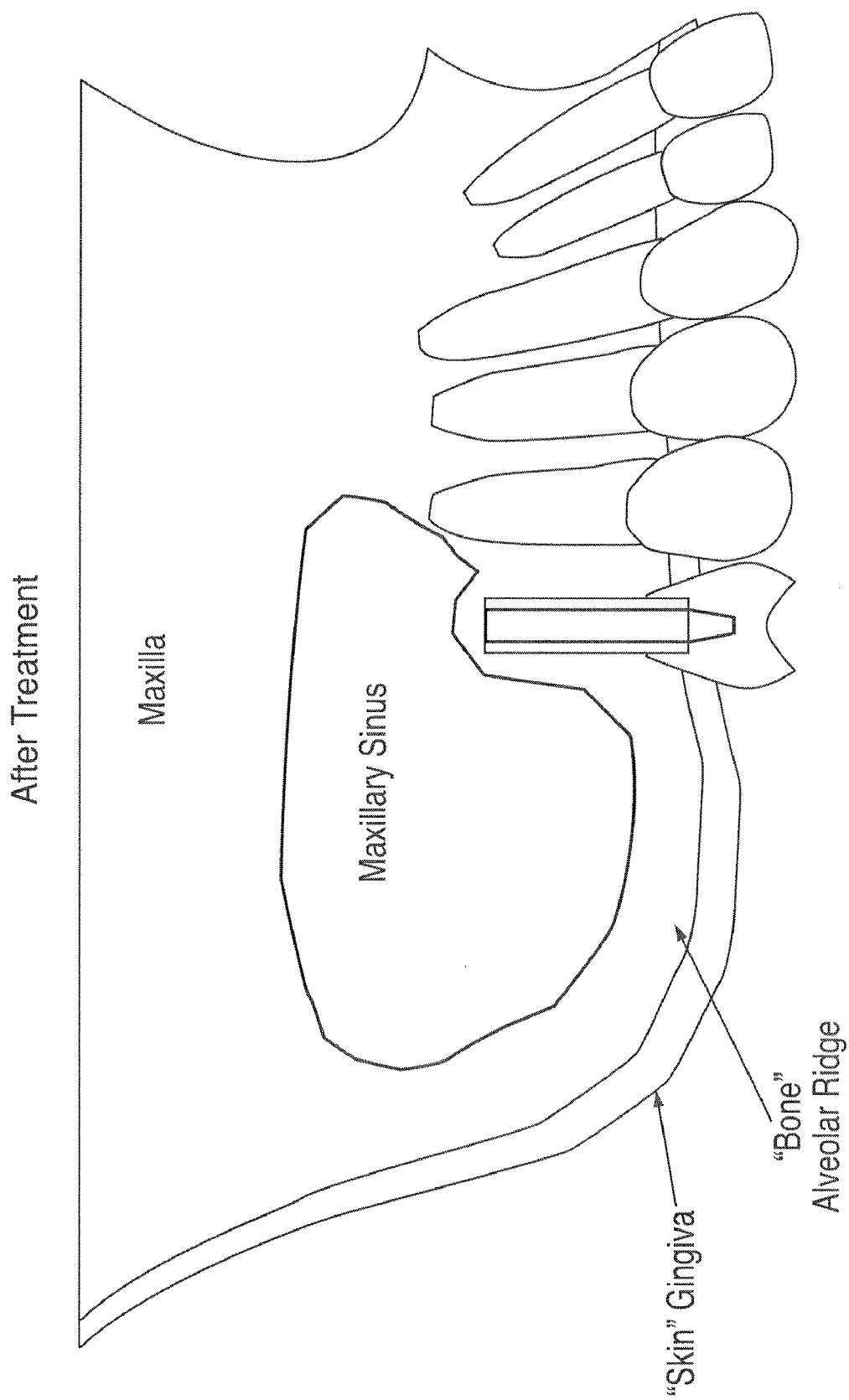

METHOD AND APPARATUS FOR PERFORMING MAXILLARY SINUS ELEVATION

RELATED APPLICATIONS

This application is a division application of U.S. application Ser. No. 11/227,687 filed Sep. 15, 2005, now U.S. Pat. No. 7,510,397 which claims priority to U.S. provisional application Ser. No. 60/619,542 filed Oct. 15, 2004 and incorporated herein by reference.

BACKGROUND OF THE INVENTION

A. Field of Invention

This invention relates generally to improvements to the delivery of drugs, particularly for osseous regeneration for the maxillary sinus. More specifically this invention provides a method and device to the elevation of the floor of the maxillary sinus to increase the amount of bone available based on using hydro-dissection to raise the subantral membrane floor of the sinus (a.k.a. the Schneiderian membrane) allowing placement of osseous regenerative materials.

B. Description of the Prior Art

Dental implants have been used in dentistry for about 20 years. They offer a tremendous benefit to patients by allowing the replacement of missing teeth. Prof. Per-ingvaar Branemark introduced the use of titanium dental implants that showed that predictable, stabile implant integration occurs when implants have sufficient contact with the surrounding bone. Initially the placement of dental implants were limited to the anterior lower jaw, as this region provided sufficient bone quantity, quality and strength to support and hold a dental implant having an effective length.

Dental implants have revolutionized the treatment of many patients who previously lost dental function as a result of losing teeth. Today's standards of care now dictate that tooth loss is best treated with dental implants which then could be used for supporting an appropriate dental appliance. The previous alternative of dental bridges is now considered an inferior alternative in comparison to dental implants.

The success of dental implants is based on a variety of factors including; surgical technique, health of the patient, operator skill and, to a significant part, sufficient bone for the placement and integration of dental implants. To that end, the replacement of the maxillary posterior teeth have presented a considerable challenge because, after the loss of maxillary posterior teeth the quality and quantity of the remaining supporting bone may be insufficient to support implants properly or reliably.

The maxillary complex is a three-dimensional bone structure composed of alveolar bone and basal bone. The teeth, and more specifically, the teeth roots are imbedded in the alveolar bone. The top of the structure forms the floor of the maxillary sinus and is covered by thin diaphanous membrane known as the subantral or Schneiderian membrane. Once a tooth is removed from the complex, the surrounding alveolar bone is frequently resorbed because of the lack of physical stimulation and support of the teeth. This leads to a loss of bone mass and a corresponding reduction in the effective height and thickness of the bone of the maxillary complex. In addition, with the loss of teeth from the upper jaw (and the maxillary complex) the compensatory enlargement of the maxillary sinus occurs that also reduces the vertical height of the remaining bone of the maxillary complex. These effects further compromise the option for dental implants to be used.

To overcome the deficiency of insufficient vertical bone mass of the maxilla, several surgical techniques have been developed to increase available bone mass for the replacement of dental implants by bone augmentation. The process includes augmenting the region with a filler or regenerative material made of natural and/or artificial (synthetic) materials by placement of these elements on the roof of the maxillary structure, under the subantral membrane so that it does not interfere with the function of the maxillary sinus.

Collectively, these procedures are known within the dental profession as "sinus elevation procedures" with the goal of increasing the vertical height available for placement of dental implants. What makes these techniques unique from other techniques, such as distraction osteogenesis, is that the bone is increased within a body cavity, i.e., the maxillary sinus cavity. The first of these surgical techniques requires a window into the maxillary sinus from a lateral and superior approach to the floor of the sinus. Great care must be taken during the entry to the sinus as it is critical not to perforate the subantral membrane that lines the sinus cavity. Bone augmentation of the maxillary sinus requires delicate dissection of the subantral membrane from the floor of the sinus. If the membrane is not properly dissected from the bone, bone augmentation may not occur, or may not be sufficient. Unintentional perforation of the subantral membrane may also lead to undesirable short and long-term consequences. If the perforation is large, for example, several millimeters in diameter, the surgeon must either abort the procedure or must use some means of containing the regenerative material placed on the floor of the sinus to encourage new bone growth. A lack of integrity of the membrane can also lead to the migration of regenerative bone materials leading to long-term chronic infections. Therefore, the maintenance of membrane integrity is of utmost importance during the elevation of the membrane to allow placement of regenerative materials with a goal of increasing bone mass in the maxilla.

Most patients and dental surgeons acknowledge that entrance into the maxillary sinus utilizing a lateral window approach (also known as the Caldwell-Luc procedure) is an invasive procedure. This technique is fraught with many risks and complications because of the limitations of healing potential in the maxillary sinus. In spite of these risks many patients undergo this procedure because of the strong desire to replace missing maxillary teeth with dental implants.

An alternative approach to the maxillary sinus from the inferior approach of the alveolar ridge utilizing solid cylindrical osteotomes was described by Dr. Summers. It is a more conservative approach and is less invasive. It was developed to eliminate the risks described above. This technique referred to as the "osteotome sinus elevation technique", and it gains access to the floor of the sinus from an inferior approach directly through the remaining alveolar ridge. The technique vertically "lifts" the floor of the sinus, or more specifically, the subantral membrane via an infracture of the bony floor and placement of bone regenerative material from an inferior approach. The bone regenerative materials are actually used to raise the subantral membrane. The infracture can be performed using solid cylindrical osteotomes with specific diameters that are vertically advanced toward the maxillary sinus producing a mechanical lifting action on the membrane. The technique has a variety of shortcomings as well, including the ability to carefully dissect (or separate) the subantral membrane from the floor of the sinus. While, this technique is safer, an overzealous use of an osteotome during the placement of the regenerative material can result in the perforation of the subantral membrane with disadvantages discussed above.

More recently several new techniques have been introduced to overcome some of the limitations of the Summers osteotome technique. The new technique also uses an inferior approach to the membrane via the alveolar ridge. One such technique was presented by Dr. Emmanuel Sotirakas using a medical syringe to raise the floor of the sinus by injecting fluid. This technique has many deficiencies owing to the inability to properly adapt a standard medical syringe to an opening created in the bone. A second technique used to elevate the subantral membrane is taught by Dr. Geraldo Nicolau Rodriguez that using a catheter balloon placed under the subantral membrane of floor of the sinus. This procedure requires an infracture of the underlying bone similar to the Summer procedure or a lateral window approach previously described. The catheter balloon is passed through the maxillary complex and the balloon is inflated. During inflation the subantral membrane is separated and forced away from the bony bed. Unfortunately, tearing or ripping of the subantral membrane may still occur and it is difficult, if not impossible, to detect it during the inflation of the balloon. In fact a perforation or tear in the membrane may take place no matter how carefully the balloon is inflated. After the membrane is separated, the balloon is withdrawn and a regenerative material is injected under the membrane, in a manner similar to the Summer technique. If a tear has occurred, the bone regenerative material may be placed unintentionally by the operator into the maxillary sinus necessitating the need for surgical removal of the regenerative material. In addition to the methods described above, an additional technique described by Dr. Leon Chen called the "Hydraulic Sinus Condensing Technique" advocates using a small round bur to gain access to the floor of the sinus exposing the membrane. Using a second larger round bur provides access which results in the exposure of the membrane to condense regenerative material below the membrane. A stream of water from a dental handpiece is used to create hydraulic pressure to elevate the subantral membrane. This technique has multiple deficiencies owing to the inability to control the pressure and forces applied to the subantral membrane owing to the lack of precision of this technique.

These alternative techniques to the lateral window approach to the maxillary sinus have evolved out of a need to develop less invasive, more conservative means of increasing the height, volume and bone mass of the maxillary alveolar ridge by elevation of the subantral membrane within the maxillary sinus and then depositing a bone regenerative material beneath the membrane to augment the available bone volume available for implant placement within the maxillary sinus.

The deficiencies and limitations of current techniques for sinus elevation relate to primarily: (1) the inability of the operator to control the infracture ("green-stick fracture) of the bony floor and lateral window of the maxillary sinus, (2) the inability to carefully separate the membrane from its physical adherence off the floor of the maxillary sinus and (3) a lack of feedback indication or confirmation for the surgeon of a perforation or tearing of the membrane prior to the placement of regenerative materials. Overcoming these previous limitations in the technique of sinus elevation will reduce infection, bleeding, swelling, pain, suffering and failure when using dental implants in the maxillary sinus.

To summarize, the following are the deficiencies of previous methods and devices:

1. Traumatic invasive surgical procedures that include extensive mucogingival flap elevation methods to gain access to the surgical site.

2. The use of instrumentation that comes into direct physical contact with the subantral membrane with the risk of perforating or tearing the membrane during separation of membrane from the floor of the sinus.

3. The need to use a infracture, i.e. "green-stick" fracture of the floor of the sinus or lateral aspect of the sinus that could once again perforate or tear the delicate subantral membrane leading to failure.

4. Using previous methods there is a lack of subjective indication or feedback to the operator that the membrane has been torn or perforated during is separation and elevation from the floor of the sinus.

5. Inability to precisely control the infracture of the bone that is required to gain access to the floor of the sinus using previous methods.

6. Inability to precisely control the force used to raise the subantral membrane.

7. Inability to precisely control the delivery of the regenerative material and to determine weather a tear or perforation of the membrane has occurred during the placement of such regenerative material.

8. Difficulty in accessing the integrity of the membrane prior to the placement of the regenerative material that will be placed on the floor of the sinus.

9. Inability to create a seal between the delivery device, such as a syringe and the prepared bony site during the elevation of the membrane and delivery of regenerative materials beneath the subantral membrane.

If regenerative materials are placed within the maxillary sinus and a perforation or tear of the subantral membrane has been caused during surgery this regenerative material will act as a foreign body within the sinus leading to ominous sequela. Failure to contain regenerative materials in the maxillary sinus often lead to the need for additional surgeries to retrieve such materials and may require extensive medical follow-up to corrective this iatrogenic outcome.

SUMMARY OF THE INVENTION

A method and device is disclosed that provides a new approach to the placement of dental implants when inadequate bone mass exists in patients' upper and lower jaws. The method and device enables dental implants to be placed more effectively within bone tissues of the oral cavity.

Moreover, a method and device is described to improve the quality and quantity of bone during the placement of dental implants. This innovation is particularly well suited to allow an increase of bone mass, including bone quality and quantity in the posterior maxilla when the elevation of the maxillary sinus floor is required. It is also well suited when poor bone quality exists in either jaw of the oral cavity.

Briefly, a system for increasing bone mass in the posterior maxilla in accordance with this invention includes one or more sleeves having various lengths and diameters. One or more of these sleeves are used in each procedure. Each sleeve is preferably cylindrical and includes a tip used to cut or otherwise form a hole into the maxillary sinus but under the subantral membrane. The sleeve is hollow to allow a fluid to be inserted under the membrane to cause it to be gently lifted from the sinus floor and form a cavity by such fluid. The cavity is then filled with a suitable material such as a material that promotes bone growth. In one embodiment, the sleeve also has cross-channels that allow the same material to be disbursed in the alveolar ridge itself to change the quality of the bone type from a less dense to a more dense bone density type.

After the material is inserted, the sleeve is removed and an implant is inserted and anchored in the alveolar ridge with portions of the implant extending into the maxillary sinus. A dental appliance or prosthesis is mounted on the implant.

Several alternate embodiments are also provided. The regenerative material and elevation of the sinus membrane can be performed as one procedure. In another such embodiment, the sleeve also acts as the implant. In still another embodiment, a balloon is used at the tip of the sleeve for separating the membrane and forming the cavity.

The sleeve overcome the deficiencies of the prior art methods and devices.

BRIEF DESCRIPTION OF THE DRAWINGS

FIG. 2 shows a cross sectional view of a sleeve constructed in accordance with this invention;

FIGS. 2A-2K show cross-sectional views of alternate tips and/or body of the sleeve of FIG. 2;

DETAILED DESCRIPTION OF THE PREFERRED EMBODIMENT

Figure 1:
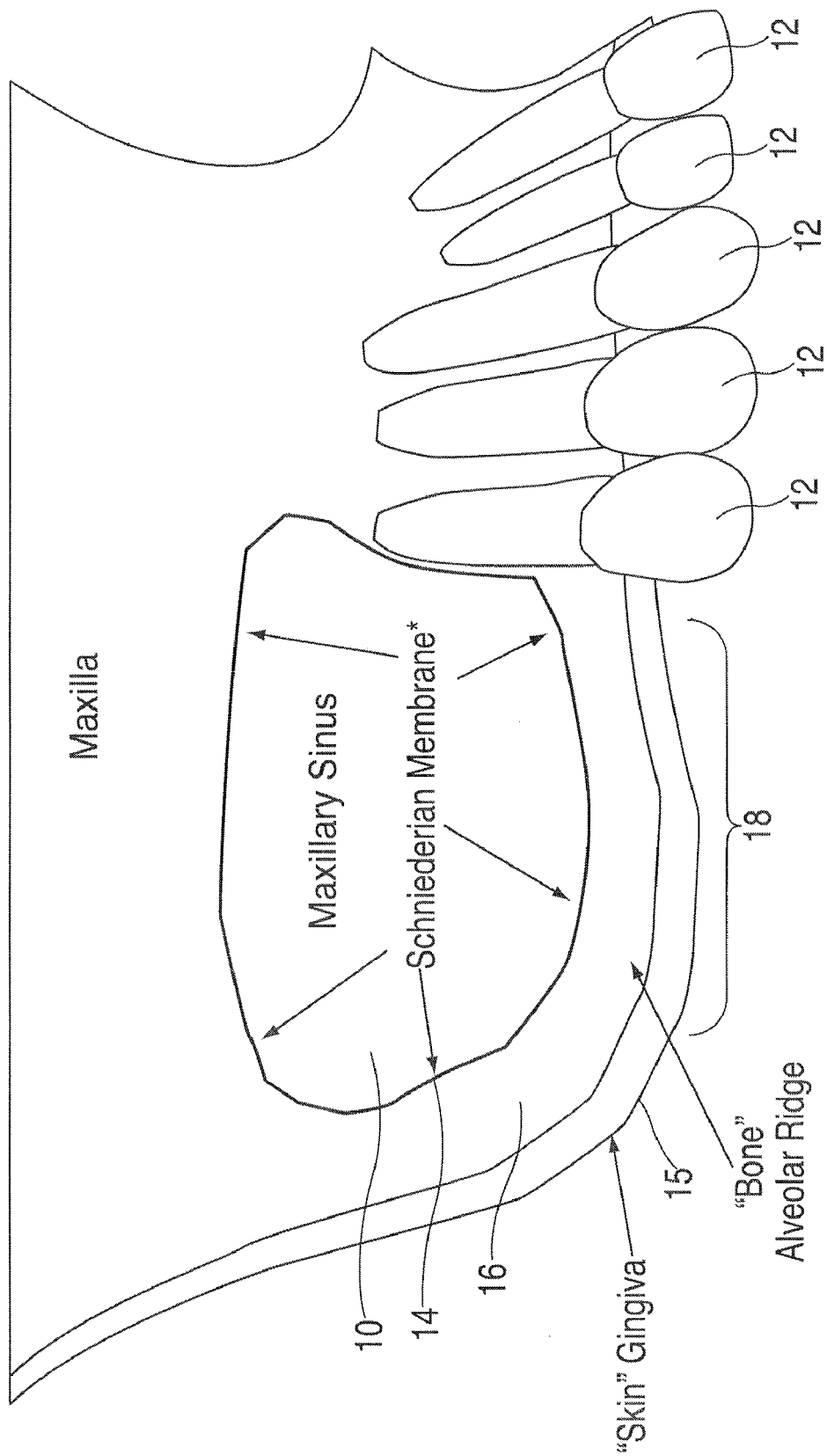
FIG. 1 shows a cross sectional view of a typical maxillary sinus for a person who has lost several molars.

FIG. 1 shows a typical cross section of the maxillary sinus 10. Several teeth 12 are seen in the Figure in a normal configuration. The maxillary sinus 10 is separated from the mouth by the alveolar ridge 16 formed of bone. The bone is covered on top by the subantral membrane 14 and on the bottom by the gingiva 15. As shown in the Figure, because this person has lost several molars, the floor of the maxillary sinus has been depressed or lowered in the area 18. As a result, the alveolar ridge 16 in this region has lost considerable bone mass and quality. Frequently, the bone in this area is porous and is not strong enough to support an implant of sufficient length and an associated final dental prosthesis. Typically, in a health person the ridge 16 in this area may be about 8 to 14 mm however, in persons who have lost their molars, the thickness of the ridge 16 may be no more than about 4 mm.

FIG. 2 shows a first embodiment of a sleeve 20 constructed in accordance with this invention. The sleeve is preferably cylindrical. As discussed in more detail below, the sleeve performs several functions. One of these functions is to raise or elevate the subantral membrane 14. The subantral membrane may be initially raised and separated from the floor of the maxillary sinus by the end of the sleeve. The membrane is raised further to create a cavity. For this purpose, an appropriate flowing material is injected through the sleeve under the membrane. This material may be a gas, e.g. air, a powder, a paste, a gel or a liquid, such as a salient solution.

A second function of the sleeve is to provide a means of cutting and/or condensing bone at the floor of the sinus prior to and during accessing to the subantral membrane.

A third function of the sleeve is to provide a means of delivering material into the bone and under the subantral membrane 14. This function is optional.

A fourth function is to form a passageway for mounting and supporting an implant.

Optionally, a fifth function is to inject stimulating substances to be delivered into and around the bone of the ridge 12. These substances can be materials and medications for bone regeneration that can be conductive, inductive or substitutions thereof including fluids and particulate matter. In this embodiment, the sleeve can be used for the delivery of bone stimulating substances into bone as well as for the elevation of the maxillary sinus membrane. Importantly, this same sleeve also serves to facilitate hydro-dissection of the maxillary membrane from the floor of the maxillary sinus, as discussed below.

The sleeve 20 includes a cylindrical body 22 with a tip 24 and a bottom 26. A channel 28 is disposed essentially coaxially within the body 22 to allow fluids to flow to the tip 24. Optionally, several cross-channels 30 are also provided to allow fluids to be delivered to the bone of the ridge as well. In FIG. 2, the tip 24 is shown as having a relatively concave or bowl shape forming a circular cutting edge 32. FIGS. 2A-2G show alternate shapes for the tip, including a square shape (FIG. 2A), a sharp or blunt convex shape (FIGS. 2B, 2C), a pointed tip (FIG. 2D). A blunter tip may prevent injuring of the subantral membrane. Moreover, as shown in FIGS. 2E-2G, the tip 24 may be formed with a narrow neck 32. FIGS. 2H-2K show alternate shapes for the whole sleeve. In FIGS. 2H, 2I the sleeve has frustoconical shapes. FIG. 2J shows a sleeve with a decreasing diameter in steps as it approaches the tip while in FIG. 2K the sleeve has a paraboloidal shape to mimic the shape of a tooth root.

Below the egresses from the cross-channels 30 (if any), the sleeve 20 is formed with an annular ring or several wings 34 that define a stop for the sleeve to limit advancement into the bone. Under the wings 34 there is provided a thumb hold 36 by which the sleeve can be held and advanced, preferably between the thumb and the index finger.

Below hold 36 there is a short connector 38 that can be used to attach the sleeve 20 to a suitable fluid supply as discussed. In a preferred embodiment, the connector 38 is sized and shaped to mate with a female or male Luer connector attached to standard tubing and optionally to a syringe or a powered drug delivery device. The bottom 26 is also formed with an entrance hole 40 communicating with the passageway 28. The outer surface of the sleeve may be provided with markers 42 to indicate the depth of the tip 24 within the ridge 16. These depth markets could be laser etched, engraved or ridges upon the surface. The markers 42 could be in the form of circular bands about the outside of the implant.

The sleeve may be designed of a metal such as titanium or an alloy such as stainless steel. Alternatively, the sleeve may be composed of plastic, composite or other suitable materials.

The cylindrical shape of the sleeve mimics the shape of a typical dental implant. Typically, the sleeve may range from 3.0 mm to 6.0 mm in diameter. The sleeve may have a variety of different length ranging from 2 mm to 14 mm, but not limited to any of these lengths or diameters. In one embodiment, a kit may be provided with a plurality of sleeves of different diameters and/or lengths. The outer surface of the sleeve can be either threaded or smooth. The texture of the surface could be polished or acid-etched, or can have other kinds of surface textures.

The sleeve could also be optionally designed with an O-ring or a tip gasket 44 (shown in FIG. 2J) to ensure an intimate fit between the sleeve and the bone ridge 16. The O-ring or tip gasket 44 could be made of a soft silicone material or any other soft material that allows adaptation and an intimate fit. It could be made of a latex or non-latex deforming material. It could also be made of a hard material such as nylon or some other material to allow intimate contact to the bony surface. The O-ring or gasket could be one or more on the surface of the sleeve. It could be positioned anywhere along the surface, most probably in an encircling pattern on the surface, as shown. The O-ring on the sleeve insures that the materials introduced under membrane 14 do not leak out.

Figure 3:
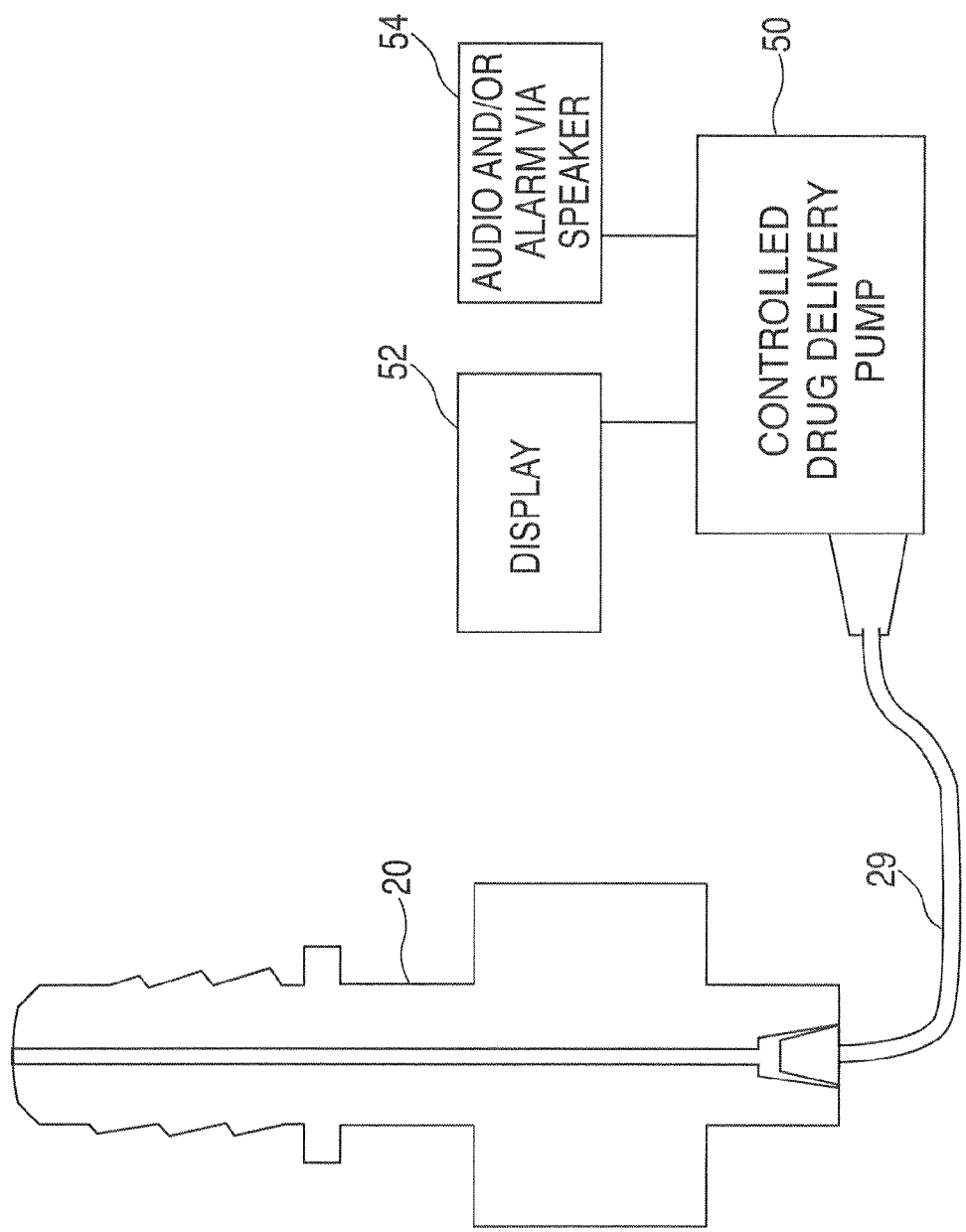
FIG. 3 shows a block diagram of a device constructed in accordance with this invention connected to a controlled drug delivery pump.

As mentioned above, the connector 38 allows a standard medical tubing set to be attached via a Luer connector. The tubing is then attached to a syringe or container that houses an appropriate material such as fluid, e.g., as a sterile saline, a drug or bone stimulating material. The sleeve may also be directly connected to the tubing that connects to a syringe or drug delivery device. Alternatively, a variety of interlocking mechanisms may be used between the tubing and the connector 38. As shown in FIG. 3, in one embodiment of the invention, a sleeve 20 is connected by tubing 29 to a controlled drug delivery device 50 such as the controlled drug delivery device described in U.S. Pat. No. 6,200,289 by Hochman et al., incorporated herein by reference. The device 50 includes, or is associated with a display 52, auditory sound that corresponds to pressure and/or an audio alarm 54. The display 50 or the sound or alarm 54 generate an output indicative of the pressure within chamber 28 as well as the fluid pressure at the tip 24.

Figure 4C:
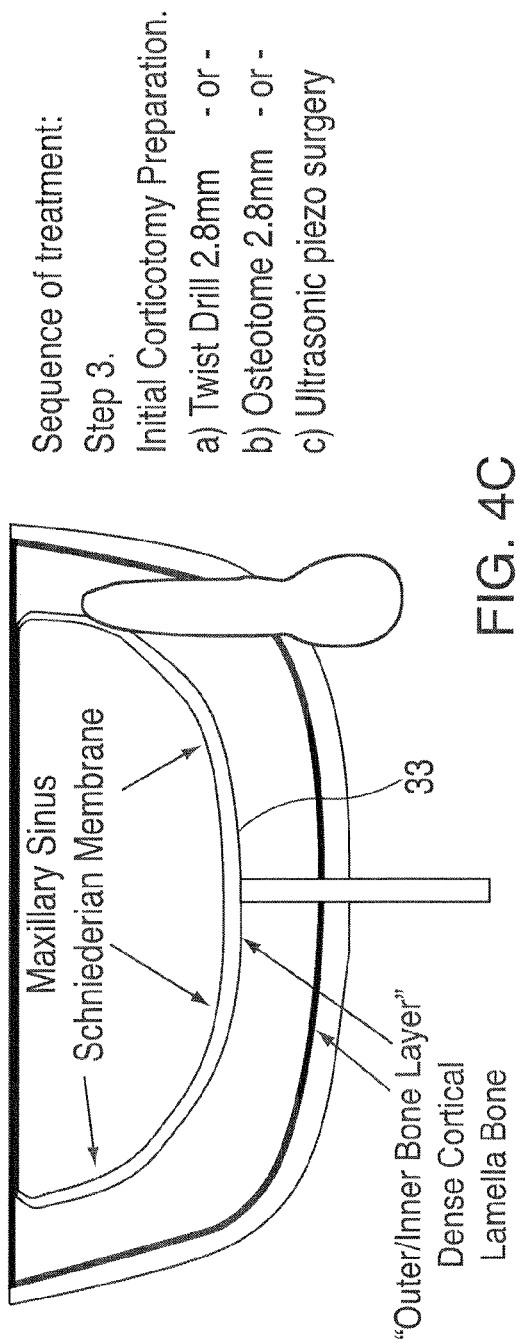
FIGS. 4A-4O show side views of the maxillary sinus during the subject process.

The method of using the sleeve is now described in conjunction with FIGS. 4A-4B. In the following example, a 10 mm sleeve having a 3.3 mm diameter is inserted into a 4 mm deep ridge. As described above, the purpose of the present invention is to increase the body mass of ridge 16 so that it can support and hold a dental implant permanently of sufficient length (8 mm to 16 mm dental implant length). After the implant has been installed, a dental appliance (such as a crown or a bridge) is mounted on the implant in the usual manner.

The first step is to make a preliminary hole through the ridge 16. As part of this step, first an incision can be made in the gingiva 15 to expose the bone forming the ridge. Alternatively, a hole can be punched in the gingival, or a round drill can be used to remove parts thereof.

Next, as shown in FIG. 4B a drill is used to make a 2 mm hole in the bone. The hole can be made using a round drill, a pilot drill, a twist drill, etc.

Figure 4D:
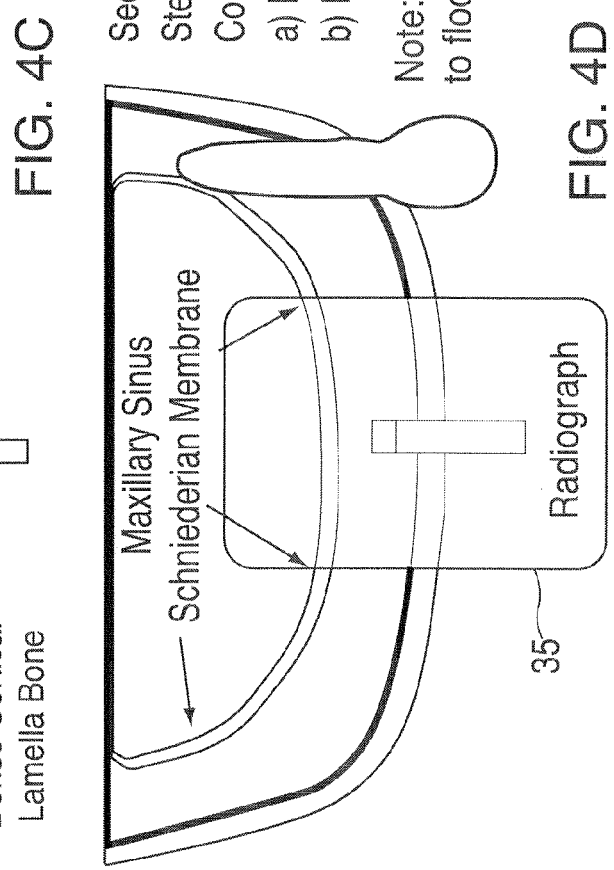

In the following step (FIG. 4C), a 2.8 mm hole is made to the subantral membrane 14. Typically, the bone 16 includes a harder bone layer 33 (known as the dense cortical lamella bone). In one embodiment, this bone layer is cut with the drill. As the surgeon approaches the membrane 14, one or more radiographs 35 are taken to show the exact position of a measuring device, i.e. depth gauge, as shown in FIG. 4D. As discussed above, it is important to insure that the membrane 14 does not get punctured or otherwise damaged during this procedure. Means for insuring that the membrane is not damaged, and for detecting membrane rupture are discussed below.

Next, in FIG. 4E sleeve 20 is inserted. Preferably the insertion is accomplished by rotating the sleeve about its longitudinal axis while simultaneously translating or advancing it. This technique may be performed manually if the surface of the sleeve 20 is smooth. Alternatively, the outer surface of the sleeve 20 is threaded and therefore rotating the sleeve causes it to automatically translate as well. The wings 34 are spaced 4 mm from the tip 24, again to insure that the membrane 14 is not damaged. The sleeve 20 is slowly inserted into the hole 37 and advanced (FIG. 4F) and rotated causing it to cut or punch through layer 33. As discussed above, in one embodiment, the hole for the sleeve 20 is precut in its entirety. In another embodiment, a drill is used to cut only a lower portion of the hole and the rest of the hole is completed by advancing the sleeve 20. The sleeve 20 has a cutting edge as described above and as it is advancing, the sleeve 20 is simultaneously cutting the bone and also condensing or contacting it both around the sleeve and ahead of thereby making the bone denser and more suitable for anchoring the implant.

Next, the sleeve is removed and a new sleeve 20' with the same 3.3 mm diameter and/or incrementally larger having a 5 mm spacing to wings 34 is inserted into the hole and the sleeve 20' is advanced further (FIG. 4G) initiating the separation of the membrane 14. In an alternate embodiment, a 5 mm (to wings 34) is used in the first place. Once, the membrane starts separating, the membrane 14 is pushed upward some more with yet another sleeve to create a space 39 between membrane 14 and the floor formed by the ridge 15.

Figure 4K:
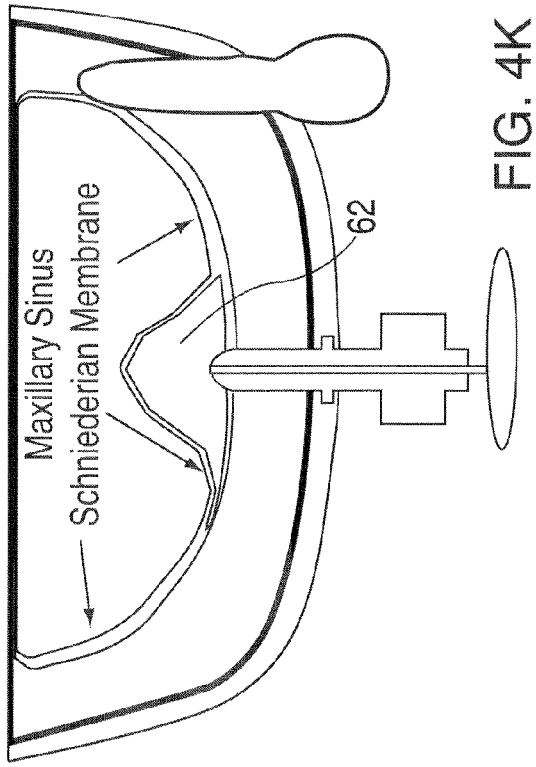
Figure 4L:
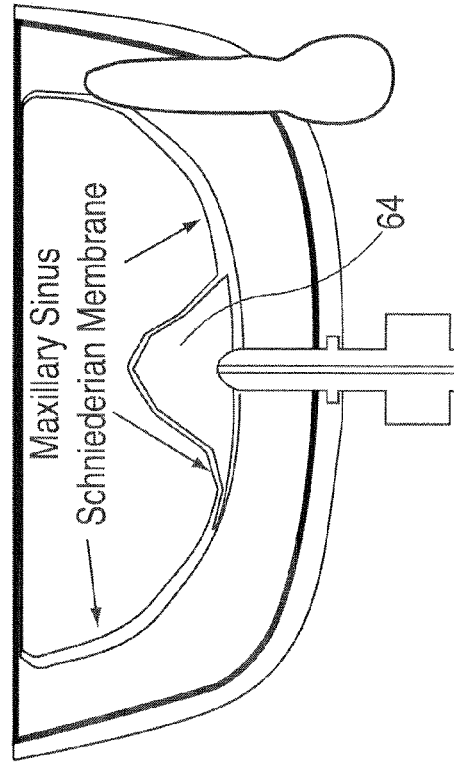

In an alternative embodiment, hydro-dissection is initiated by connecting the sleeve 20' to a manual syringe or a drug delivery device as shown in FIG. 3 and causing a sterile saline solution or other liquid into channel 28. The liquid causes the membrane to rise some more generating a cavity 62 under the membrane 14, as shown in FIGS. 4H, 4I and 4J. Preferably, sufficient fluid is pumped under the membrane so that the cavity 62 reaches between 4 mm to 8 mm to provide a total vertical height of 8 mm to 16 mm, a greater bone mass may also be created utilizing this same technique. An alternative embodiment of creating a greater bone mass may also be accomplished by utilizing a specific measured volume of the appropriate flowing material measured from within the drug delivery system selected for use. A volume 15 cc is provided as an example but not be limited to, the range is only limited by the space available within the sinus cavity. The fluid can be pumped into the sleeve after the sleeve has pushed the membrane up somewhat to start the hydro-dissection process. Next, as shown in FIG. 4K, the saline solution is drained from cavity 62 and in the next step shown in FIG. 4L a regenerative material 64 is used to replace it in the cavity 12, again, using a syringe, the device of FIG. 3, or other known means. The regenerative material 64 is a known regenerative material including allographs, autogeneous bone grafts, xenografts. Such materials may include natural materials, artificial materials, or a mixture thereof. Examples include freeze dried allograph bone, Emdogain (Straumann ITI, Inc.), Pepgen 15 (Dentsply, Inc) or any other bone stimulation substance derived from the patient's blood or other biological sources such as Platelet Rich Plasma (PRP), or a variety of growth factors such as; insulin-like growth factor-1 (IGF-1), a transforming growth factor-.beta. (TGF-.beta.), a basic fibroblast growth factor (bFGF), a cartilage-inducing factor-A, a cartilage-inducing factor-B, an osteoid-inducing factor, a collagen growth factor and osteogeninbone morphogenic proteins (BMP).

These materials promote bone grow in and around cavity 62. In order to strengthened the existing bone structure of the ridge itself, especially around the sleeve, one or more cross-channels are provided in the sleeve to allow the bone stimulating material to dissipate directly into the porous bone of the ridge.

In one embodiment of the invention, the regenerative material is pumped directly through the sleeve 20. In another embodiment of the invention, the sleeve 20 is removed, and the material 64 is pumped into the cavity 62 (and the bone of the ridge 16) through the hole 37. In yet another embodiment of the invention, the step of injecting the salient solution to pump up cavity 62 is omitted and the material 64 is pumped in and used to raise the membrane 14 and to generate cavity 62.

In another embodiment the sleeve is pressurized as it is advanced through the bone. As soon as the top surface of the bone is breached, fluid from the sleeve rises under the membrane and causes it to separate from bone.

As discussed above, one major concern during the steps of hydro-dissecting is that the membrane 14 could be damaged or ruptured, because obviously, if this occurs the material 64 should not be pumped into the cavity 62. However, since the membrane 14 is insubstantial, it is difficult to determine whether it has been damaged or not. Therefore, in one embodiment, during hydro-dissection, the liquid pressure within the channel 28 and the cavity 62 is continuously monitored. For example, if the device of FIG. 3 is used, then this device automatically determines this pressure from measurements made within the device 50 itself. The pressure can be displayed on the screen 52 or is provided to the surgeon as an audible signal. This audible signal may be a sound or spoken words. The surgeon either listens to corresponding information that provides fluid pressure during hydro-dissection or can watch this pressure during hydro-dissection and can decrease the fluid flow into the cavity 62 if this pressure approaches a threshold or safety level. This level may be about 2 psi to 10 psi. Moreover, a sudden drop in the pressure during continuous fluid flow is a clear indication of a rupture of the membrane 14. This event is indicated on the screen 52 and/or the audio alarm 54. If a rupture occurs, the procedure is halted, and the patient is sent home for several days to allow the membrane to heal. During this time, the sleeve 20 can stay in place thereby allowing the process to be readily resumed at a later time.

Monitoring of the pressure within the channel 28 or cavity 62 can be performed during the injection of the salient solution, the injection of material 64 or both.

Alternatively, monitoring of the pressure can also be achieved using a "loss of resistance" method in which a conventional syringe or glass (epidural syringe) is used. If a rupture of the subantral membrane occurs the surgeon will feel a loss of resistance of the plunger of the medical syringe immediately and an appropriate action can be taken. Once the syringe is used to raise the membrane an appropriate material can be placed with or without the syringe.

Additionally, monitoring of the pressure with a syringe with integrated manometer such as the Viceroy® Inflation Syringe from (Merit Medical, Inc.) that allows pressure monitoring directly from a gauge affixed to the syringe or other syringe devices incorporating a pressure sensing/monitoring like device capability as such as Hadzic, et. al. describes in U.S. Pat. No. 6,866,648. Devices presenting alternative means to monitor and sense pressure from a drug delivery vessel or syringe.

Figure 4M:
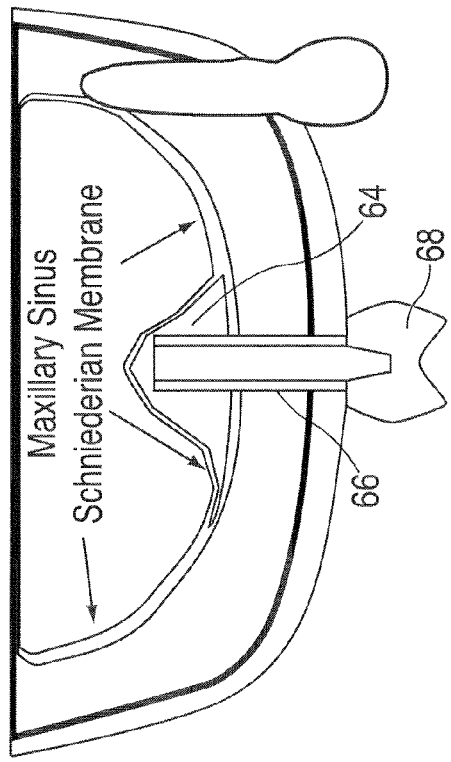
Figure 4N:
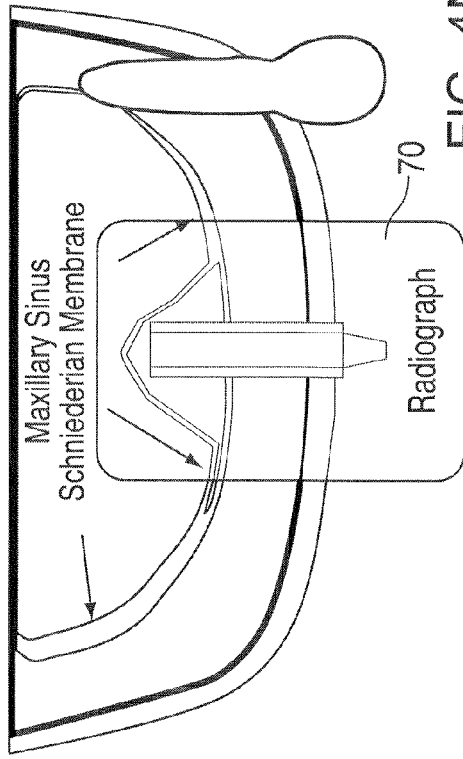

After a sufficient amount of material 64 is injected into the cavity 62, the sleeve 20 is removed and replaced with a standard implant 66 (See FIG. 4M). A crown or other appliance 68 is then affixed to the implant 66. As shown in FIG. 4N, the position of the implant and the placement of the material 64 is checked either before or after the appliance 68 is installed.

In an alternate embodiment, either after the material 64 is inserted, after the sleeve 20 is removed, or after the implant 66 is installed the process is halted for a period of time, example several weeks or months to allow the sinus and the ridge 12 to heal itself, for additional bone material to grow at the site thereby increasing the bone mass, and/or to allow material 64 to set.

After awhile, the bone regrows around the material 64 and the implant thereby effectively increases the thickness of the ridge 12, as illustrated in FIG. 4O.

Several other alternatives may be used to practice the invention as well. In one embodiment, the sleeve 20 may be placed with a delivery tool (not shown) that can attach to the sleeve temporarily to transfer it into the patient's mouth without directly handling it. The tool also allows the sleeve to be inserted or screwed-in providing mechanical advantages of placement.

Figure 5B:
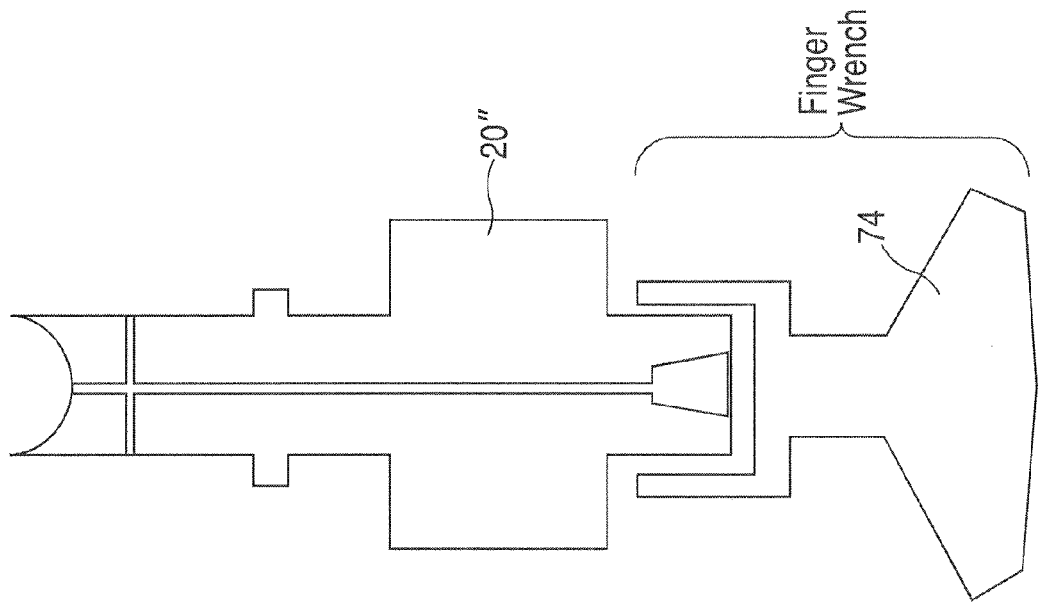
FIGS. 5A and 5B show embodiments of the sleeve modified so that it can be installed using a standard dental wrench.
Figure 5A:
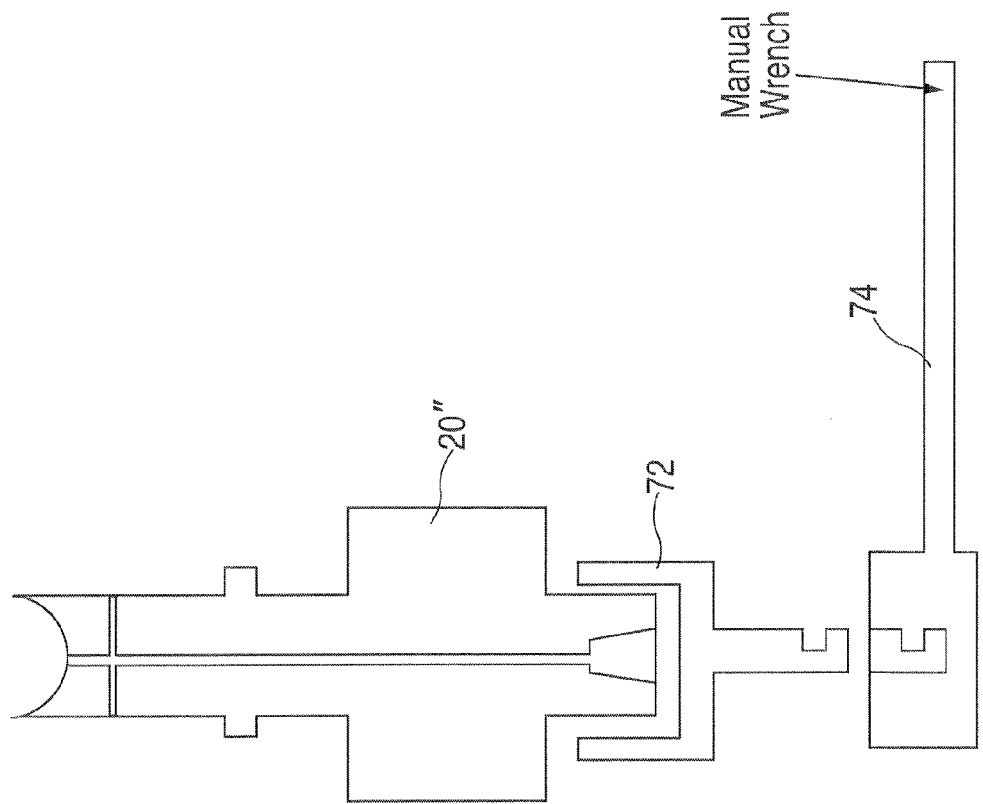

As illustrated in FIG. 5A, a sleeve 20" may be designed so that its connector 38 is shaped to fit into a latch adapter 72. During the insertion and/or removal of the sleeve, the adapter 72 is positioned over the bottom of the sleeve 20" and then a standard manual wrench 74 is used to advance or retract the sleeve from the ridge 12.

Alternatively, the latch adapter 72 may also be designed so that it will fit directly into a rotary dental hand piece or manual wrench commonly used in dentistry, as already shown in FIG. 5A. The sleeve delivery tool may also be designed in a "Ratchet type" form to allow the sleeve to be ratcheted into the bone of a patient.

As illustrated in FIG. 5B, a sleeve 20" may be designed so that its connector 38 is shaped to fit into a manual wrench adapter 74. During the insertion and/or removal of the sleeve, the adapter 74 is positioned over the bottom of the sleeve 20" and is used to advance with the thumb and index finger to allow for greater mechanical force and manipulation as the sleeve 20" is placed into and removed from the ridge 12.

In another embodiment of the invention, instead of using a separate standard implant, the sleeve 20 itself is designed to accept on its lower portion a dental appliance. In this embodiment, the steps shown in FIG. 4M are omitted, and the sleeve 20 is not removed but instead, the device 68 is mounted on the sleeve. Hence, in this embodiment the sleeve 20 acts as an implant 66 as well.

As discussed above, the sleeve 20 can be inserted into hole 37 by several means, such as tapping or screwing. If screwing is used, then the outer surface of the sleeve is threaded as it 78 in FIG. 6A.

Figure 6C:
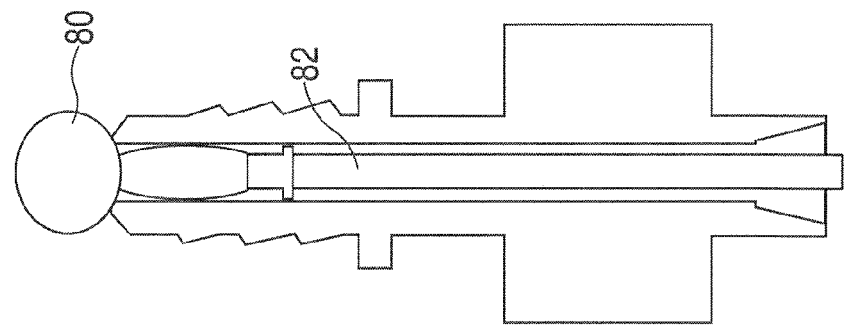
FIGS. 6A-6D show an embodiment of the invention wherein a balloon is used to perform hydro-dissection of the subantral membrane.
Figure 6B:
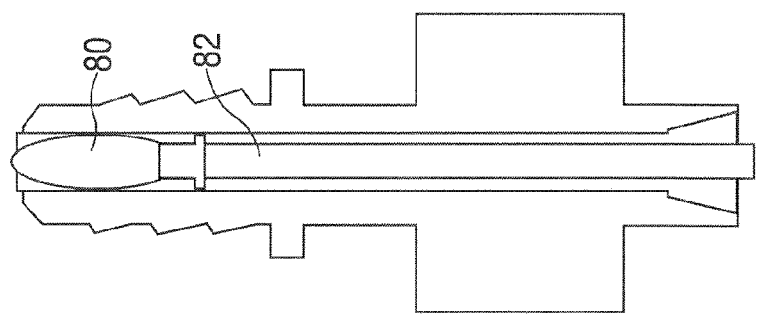
Figure 6A:
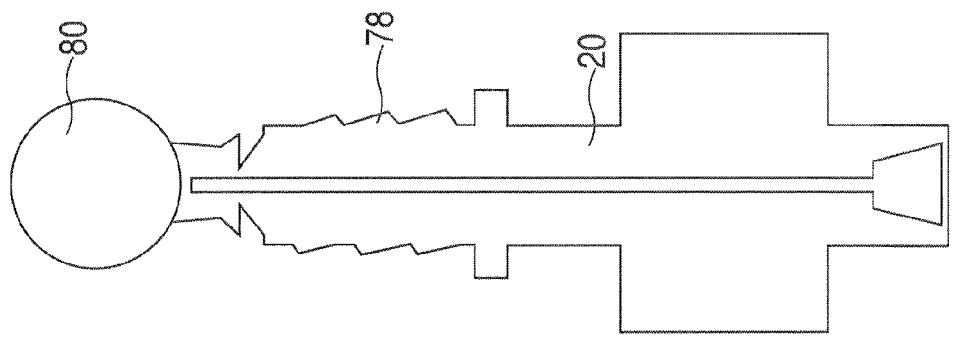

An alternate embodiment, a balloon is used for performing the dissection. In the embodiment shown in FIG. 6A, the sleeve 20 is provided with the narrow neck and flared tip shown in FIG. 2E. This shape allows a balloon 80 to be mounted externally onto the sleeve. In this embodiment, the sleeve 20 is first used to make the whole 37 and, optionally, to separate the subantral membrane from the sinus floor. Then the sleeve 20 is removed, the balloon 80 is mounted on the sleeve, and the sleeve is replaced with the balloon mounted thereon as shown in FIG. 6A. The connector 38 is then coupled to an appropriate source of air or salient solution and the balloon is blown up thereby implementing the membrane separation from the floor of the sinus.

Figure 6D:
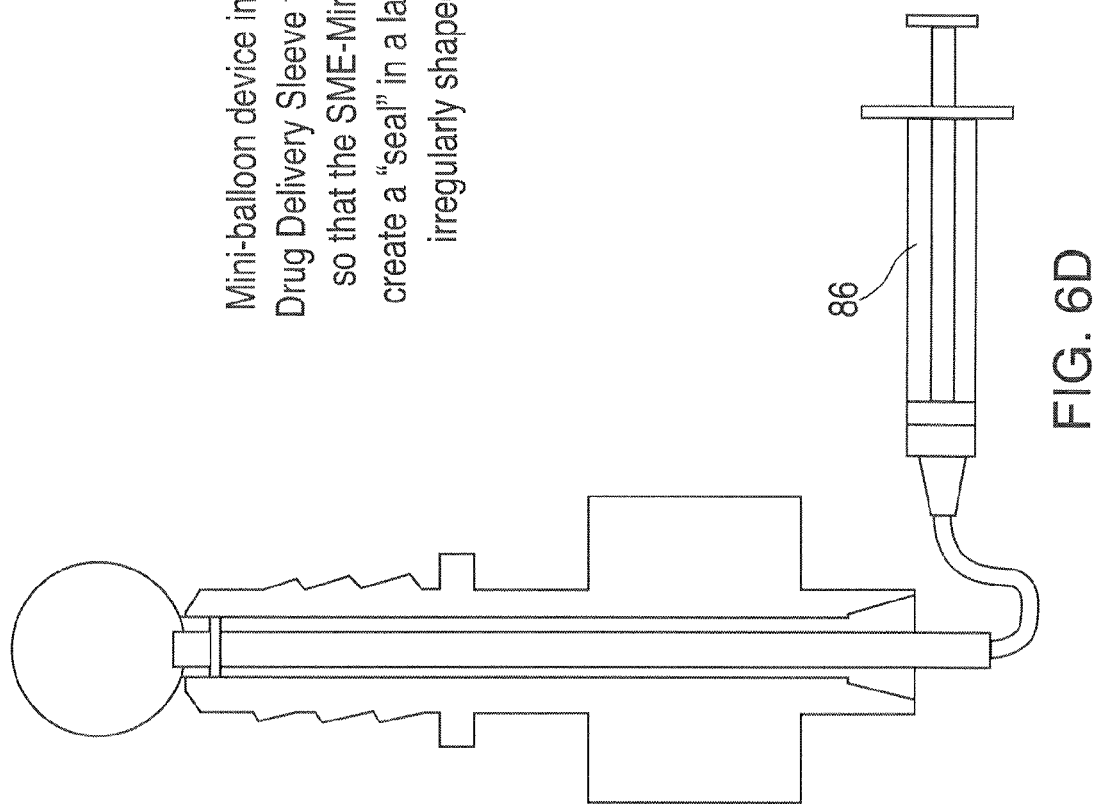

In another embodiment, the balloon 80 is mounted at the end of a catheter or stylet 82. The balloon 80 is then inserted through the channel 28 until it reaches the desired site as shown in FIGS. 6B and 6C. The catheter 82 is connected to a source, such as a syringe 86 shown in FIG. 6D and then inflated for separation of the subantral membrane from the bone.

Figure 7A:
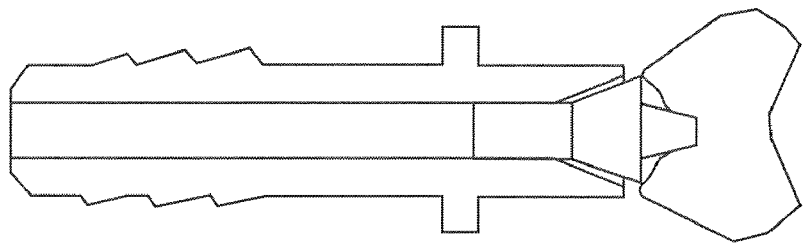
FIGS. 7A-7C show a sleeve constructed in accordance with this invention being converted into an implant and receiving a dental prosthesis.
Figure 7B:
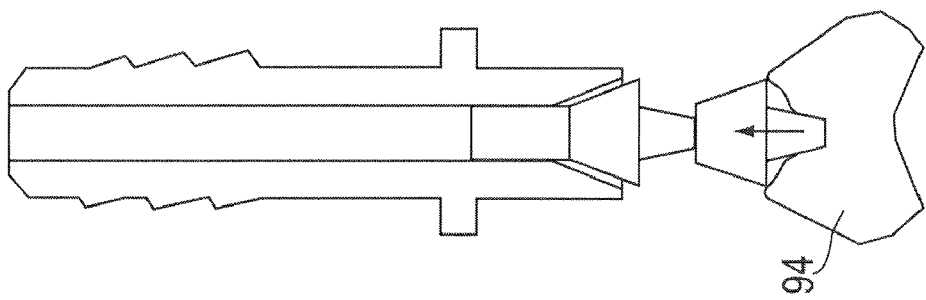
Figure 7C:
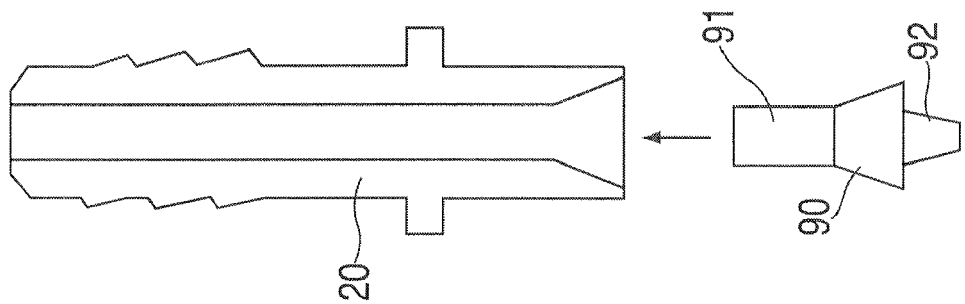

FIGS. 7A-7C shows how a sleeve 20 constructed in accordance with this invention is modified to act as an implant. As shown in FIG. 7A, first an abutment 90 is attached to the sleeve. More particularly, the abutment 90, has a cylindrical end 91 and a conical end 92 interconnected by a portion 93 having a slanged sidewall. The end 91 and portion 93 fit into the central channel 28 of sleeve 20. The abutment 90 is secured to the sleeve 20 by using an adhesive or cement. Alternatively, the abutment is secured by an interference fit, or by providing a threaded engagement therebetween.

Once the abutment is firmly attached to the sleeve, a prosthesis 94 is then attached to the abutment in the usual manner as shown in FIG. 7B. FIG. 7 shows the prosthesis 94 mounted on the sleeve 20.

To summarize, the subject device provides several improvements and advantages over the prior art to enable the improvement of bone quantity and quality and increase bone mass in the upper jaw for the placement of dental implants. Some of these advantages include:

A means to allow the use of medications and bone stimulating substances to be placed in and around existing bone, and more specifically, the alveolar ridge. The bone stimulating substances can be placed prior to, during or after dental implant placement.

A means to raise/elevate the sinuous floor of the maxillary sinus without damaging the subantral membrane. The membrane is raised off of the bony surface by hydrostatic pressure that can be delivered through a sleeve. During this process, the exit pressure from the sleeve is monitored to insure that it does not increase beyond a threshold level. A drop in the exit pressure is indicative of a ruptured membrane. Medications including bone stimulating substances can be delivered through both the removable sleeve.

In one embodiment, a balloon catheter is placed through the sleeve to allow additional space to be created around the implant prior to the placement of medications or bone stimulating substances. The ballooning technique will provide additional space for the placement of materials. In the maxilla, additional space may be created by elevation of the sinuous floor. The method and device herein disclosed for the first time presents a method and device that allows a multipurpose sleeve to be placed in the bone forming the alveolar ridge. The advantage allows an adequate and precise seal between the delivery system and the prepared bony site thus allowing precise and adequate pressure to be used to effectively control the delivery of such biological products within the alveolar ridge and sinus cavity. The advantages of this system is that it minimizes the risks of damage to tissues.

The seat platform or Seating Collar design ensures that the Drug Delivery Dental Implant Sleeve or Dental Implant will be placed to a specified depth within the bone. The Seat will prevent the sleeve or implant from accidentally being advanced into the maxillary sinus requiring a subsequent surgical procedure to be performed to remove the implant from within the maxillary sinus. The Seat also ensures that during the initial elevation of the sinus from the bony floor that the Dental Implant or Sleeve will not tear or damage the membrane by premature contact to the membrane.

Numerous modifications may be made to the invention without departing from its scope as defined in the appended claims.

The invention claimed is:

1. A method for Sinus Elevation comprising the steps of:
   providing a hole through a portion of the alveolar ridge to a point below the subantral membrane;
   inserting a sleeve into the hole;
   introducing a flowing material through said sleeve, said flowing material being selected from the group consisting of a gas, a liquid, a gel, a paste and a powder;
   monitoring a pressure of said flowing material as it is being introduced;
   detecting when said pressure falls below a predetermined threshold, said predetermined threshold being selected to indicate a breach of said membrane; and
   generating an indication when said breach is detected.

2. The method of claim 1 wherein said filler is injected using a hand-operated syringe.

3. The method of claim 1 wherein said filler is injected using an automated injection device.

4. The method of claim 1 further comprising changing said sleeve with an implant.

5. The method of claim 4 further comprising mounting a dental prosthesis on said implant.

6. The method of claim 1 wherein said sleeve includes a central passage for injecting said flowing material.

7. The method of claim 1 wherein said sleeve includes cross-passages leading said flowing material into the alveolar ridge.

8. A method for Sinus Elevation comprising the steps of:
   providing a hole through a portion of the alveolar ridge to a point below the subantral membrane;
   inserting a sleeve into the hole;
   introducing a flowing material with a hand-held syringe through said sleeve, said flowing material being selected from the group consisting of a gas, a liquid, a gel, a paste and a powder;
   monitoring a pressure of said flowing material as it is being introduced;
   detecting when said pressure falls below a predetermined threshold, said predetermined threshold being selected to indicate a breach of said membrane; and
   generating an indication when said breach is detected.

* * * * *